United States Patent
Nikolov et al.

(10) Patent No.: US 11,372,103 B2
(45) Date of Patent: Jun. 28, 2022

(54) ULTRASOUND IMAGING WITH MULTIPLE SINGLE-ELEMENT TRANSDUCERS AND ULTRASOUND SIGNAL PROPAGATION CORRECTION USING DELAY AND SUM BEAMFORMING BASED ON A CROSS-CORRELATION FUNCTION

(71) Applicant: B-K Medical Aps, Herlev (DK)

(72) Inventors: Svetoslav Ivanov Nikolov, Farum (DK); Jens Munk Hansen, Copenhagen (DK)

(73) Assignee: B-K MEDICAL APS, Herlev (DK)

( * ) Notice: Subject to any disclaimer, the term of this patent is extended or adjusted under 35 U.S.C. 154(b) by 683 days.

(21) Appl. No.: 16/081,228

(22) PCT Filed: Mar. 1, 2016

(86) PCT No.: PCT/IB2016/051124
§ 371 (c)(1),
(2) Date: Aug. 30, 2018

(87) PCT Pub. No.: WO2017/149352
PCT Pub. Date: Sep. 8, 2017

(65) Prior Publication Data
US 2019/0072671 A1    Mar. 7, 2019

(51) Int. Cl.
*G01S 15/89* (2006.01)
*A61B 8/12* (2006.01)
(Continued)

(52) U.S. Cl.
CPC ............ *G01S 15/8993* (2013.01); *A61B 8/12* (2013.01); *A61B 8/4477* (2013.01);
(Continued)

(58) Field of Classification Search
CPC ............ G01S 15/8993; G01S 7/52046; G01S 7/5205; G01S 15/8945; G01S 15/8952;
(Continued)

(56) References Cited

U.S. PATENT DOCUMENTS 6,120,455 A     9/2000  Teo
6,123,670 A *   9/2000  Mo ........................ A61B 8/469
                                                                600/447

(Continued)

FOREIGN PATENT DOCUMENTS

WO    2008039793 A1    4/2008

OTHER PUBLICATIONS

Andresen, Henrik & Nikolov, S.I. & Jensen, Jørgen. (2011). Synthetic Aperture Focusing for a Single-Element Transducer Undergoing Helical Motion. IEEE transactions on ultrasonics, ferroelectrics, and frequency control. 58. 935-43. 10.1109/TUFFC.2011.1894. (Year: 2011).*

(Continued)

*Primary Examiner* — Christopher Koharski
*Assistant Examiner* — Richmond J Van Winter
(74) *Attorney, Agent, or Firm* — Daugherty & Del Zoppo, Co. LPA

(57) ABSTRACT

A method includes receiving first electrical signals from a first single-element transducer ($112_1$) and second electrical signals from a second single-element transducer ($112_2$). The transducers are disposed on a shaft (110), which has a longitudinal axis (200), of an ultrasound imaging probe (102) with transducing sides disposed transverse to and facing away from the longitudinal axis. The transducers are angularly offset from each other on the shaft by a non-zero angle. The transducers are operated at first and second different cutoff frequencies. The shaft concurrently translates and rotates while the transducers receive the first and (Continued)

second ultrasound signals. The method further includes delay and sum beamforming, with first and second beamformers ($120_1$, $120_2$), the first and second electrical signals, respectively via different processing chains ($712_1$, $712_2$), employing an adaptive synthetic aperture technique, producing first and second images. The method further includes combining the first and second images, creating a final image, and displaying the final image.

26 Claims, 10 Drawing Sheets

(51) Int. Cl.
    *A61B 8/00*     (2006.01)
    *G01S 7/52*     (2006.01)

(52) U.S. Cl.
    CPC ........ *G01S 7/5205* (2013.01); *G01S 7/52046* (2013.01); *G01S 7/52052* (2013.01); *G01S 7/52077* (2013.01); *G01S 15/894* (2013.01); *G01S 15/8945* (2013.01); *G01S 15/8952* (2013.01); *G01S 15/8997* (2013.01)

(58) Field of Classification Search
    CPC ............. G01S 15/8997; G01S 7/52052; G01S 7/52077; G01S 15/894; G01S 15/8936; G01S 15/8934; A61B 8/12; A61B 8/4477; A61B 8/4494; G11B 20/10398; H03M 1/0836; H04L 43/087; H40R 2430/23
    See application file for complete search history.

(56) References Cited

U.S. PATENT DOCUMENTS

| | | |
|---|---|---|
| 6,159,153 A | 12/2000 | Dubberstein et al. |
| 2004/0225221 A1* | 11/2004 | Olsson ................ A61B 8/5238 600/447 |
| 2006/0245601 A1* | 11/2006 | Michaud ................ H04R 3/005 381/92 |
| 2008/0110263 A1* | 5/2008 | Klessel ............... G01S 7/52085 73/602 |
| 2009/0067699 A1* | 3/2009 | Clark ..................... A61B 8/463 382/131 |
| 2009/0304246 A1* | 12/2009 | Walker ................ G06K 9/0051 382/128 |
| 2010/0152590 A1 | 6/2010 | Moore et al. |
| 2013/0102865 A1* | 4/2013 | Man ................... G01N 21/1702 600/328 |
| 2014/0288426 A1 | 9/2014 | Ebisawa |
| 2016/0143614 A1* | 5/2016 | Huang .................. A61B 8/085 600/424 |
| 2016/0157828 A1* | 6/2016 | Sumi ..................... G01N 29/262 702/189 |
| 2018/0303545 A1* | 10/2018 | Lupotti ................ A61B 8/4477 |
| 2018/0310915 A1* | 11/2018 | Maruyama ........... A61B 8/4494 |

OTHER PUBLICATIONS

International Search Report for PCT/IB2016/051124 published as WO2017149352 on Sep. 8, 2017.
Henrik Andresen et al. Synthetic aperture focusing for a single-element transducer undergoing helical motion, IEEE Trans. on Ultrasonics, Ferroelectrics and Frequency Control, vol. 58, No. 5, pp. 935-943, May 1, 2011.
B-K Medical: 20R3 Transducer—User Guide, pp. 1-26, XP055321000, Retrieved from the internet: URL: www.okultrasound.com/filedepot_download/965/307, Aug. 2015.
Henrik Andresen, Synthetic Aperture Beamforming in Ultrasound using Moving Arrays, Dissertation, May 2009.
Bastien Denarie, Real-time 3-D echocardiography: challenges of parallel transmission and acquisition, Thesis for the degree of Philosophiae Doctor, Trondheim, Nov. 2013.
Jacob Kortbek, Synthetic Aperture Sequential Beamforming and other Beamforming Techniques in Ultrasound Imaging 2008.
Andresen, Henrik Stensby, et al., Synthetic Aperture Focusing for a Single Element Transducer undergoing Helix Motion, IEEE Transactions on Ultrasonics, Ferroelectrics and Frequency Control, 2011, Downloaded from orbit.dtu.dk on: Jan. 6, 2016.

\* cited by examiner

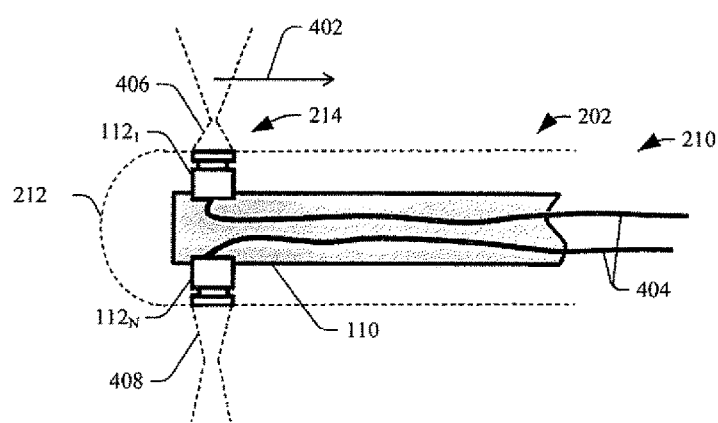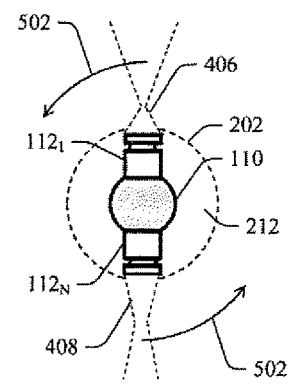
FIGURE 4
FIGURE 5
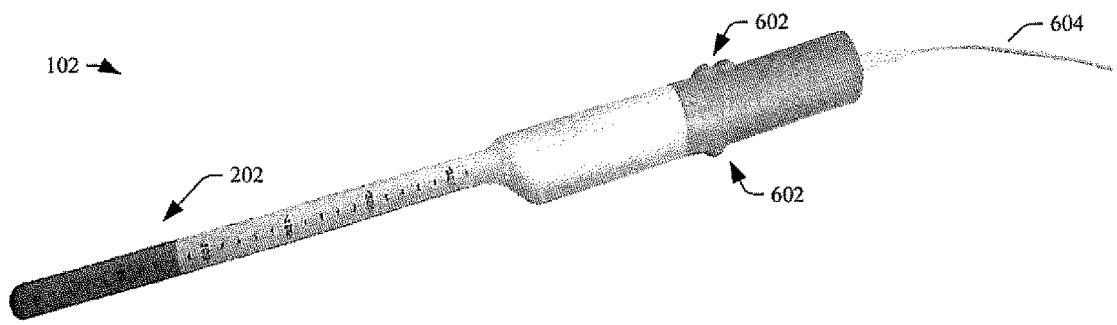
FIGURE 6

ULTRASOUND IMAGING WITH MULTIPLE SINGLE-ELEMENT TRANSDUCERS AND ULTRASOUND SIGNAL PROPAGATION CORRECTION USING DELAY AND SUM BEAMFORMING BASED ON A CROSS-CORRELATION FUNCTION

RELATED APPLICATION

This application is a national filing of PCT application Serial No. PCT/M2016/051124, filed Mar. 1, 2016, published as WO2017/149352 on Sep. 8, 2017. This application claims priority to PCT application Serial No. PCT/IB2016/051124, published as WO2017/149352 on Sep. 8, 2017.

TECHNICAL FIELD

The following generally relates to ultrasound imaging and more particularly to three-dimensional (3-D) ultrasound imaging with multiple, single-element transducers and ultrasound signal propagation correction.

BACKGROUND

Ultrasound imaging can be used to provide one or more real-time images of information about the interior of a subject, such as an organ, tissue, blood, etc., or an object. This includes two-dimensional and/or three-dimensional images. Three-dimensional probes acquire data that can be processed to generate three-dimensional images. One such probe includes two, single-element transducers disposed on a shaft one hundred and eighty degrees apart. The shaft is configured to translate and rotate, which translates and rotates the two, single-element transducers. Concurrently translating and rotating the shaft moves the two, single-element transducers along a helix trajectory during data acquisition, collecting data for three-dimensional imaging.

When the two, single-element transducers are operated at two different center frequencies and focused at two different depths, a sonographer can choose whether to use the higher frequency for nearer field imaging, or the lower frequency for farer field imaging. Synthetic aperture focusing has been used to increase image quality of images acquired with a single-element transducer. However, the mechanical movement of the two, single-element transducer probe gives rise to jitter, and jitter and along with transducer acceleration result in a calculated transducer position that is different from the actual transducer position. Unfortunately, this difference introduces error in the delay in delay and sum beamforming, which can degrade image quality.

SUMMARY

Aspects of the application address the above matters, and others.

In one aspect, a method is for ultrasound imaging with a first single-element transducer and a second single-element transducer. The first and second single-element transducers are disposed on an ultrasound probe shaft, which has a longitudinal axis, with transducing sides disposed transverse to and facing away from the longitudinal axis. The first and second single-element transducers are angularly offset from each other on the shaft by a non-zero angle. The method includes operating the first and second single-element transducers at first and second different cutoff frequencies, and concurrently translating and rotating the shaft, moving the first and second single-element transducers along a helical path while the first and second single-element transducers acquire first and second echo signals. The method further includes receiving first electrical signals from the first single-element transducer, wherein the first electrical signals are indicative of the first echo signals, and receiving second electrical signals from the second single-element transducer, wherein the second electrical signals are indicative of the second echo signals. The method further includes delay and sum beamforming, with first and second adaptive synthetic aperture focusing beamformers, the first and second electrical signals, respectively via different processing chains, employing adaptive synthetic aperture focusing, producing first and second images. The method further includes combining the first and second images, creating a final image and displaying the final image.

In another aspect, an ultrasound imaging system includes a probe with an elongate shaft, a drive assembly coupled to the elongate shaft and configured to translate and rotate the shaft, and at least first and second single-element transducers disposed at an end region of the shaft angularly separated from each other by an angle in a range between 60 and 180 degrees. The at least first and second single-element transducers transmit and receive in a direction transverse to the elongate shaft and have different center frequencies, and respectively generate first and second electrical signals. The ultrasound imaging system further includes a console with delay and sum beamformer configured to process the first and second electrical signals respectively through different processing chains, wherein the different processing chains respectively include first and second adaptive synthetic aperture focusing beamformers configured to employ adaptive synthetic aperture focusing to produce first and second images. The ultrasound imaging system further includes an image combiner that combines the first and second images and displays the combined image on a display.

In another aspect, an apparatus includes a delay and sum beamformer configured to process first and second electrical signals respectively through different processing chains, wherein the different processing chains respectively include first and second adaptive synthetic aperture focusing beamformers configured to employ adaptive synthetic aperture focusing to produce first and second images. The first electrical signals are received from a first single-element transducer. The first electrical signals are indicative of first ultrasound signals, and receiving second electrical signals are received from a second single-element transducer. The second electrical signals are indicative of second ultrasound signals. The first and second single-element transducers are disposed on a shaft, which has a longitudinal axis, of an ultrasound imaging probe with transducing sides disposed transverse to and facing away from the longitudinal axis. The first and second single-element transducers are angularly offset from each other on the shaft by a non-zero angle. The first and second single-element transducers are operated at first and second different cutoff frequencies. The shaft concurrently translates and rotates while the first and second single-element transducers receive the first and second ultrasound signals. The apparatus further includes an image combiner that combines the first and second images and displays the combined image on a display.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which:

FIG. 4 schematically illustrates an example of the three-dimensional ultrasound probe with the at least two, single-element transducers translating from the extended position to the retracted position;

FIG. 5 schematically illustrates an example of the three-dimensional ultrasound probe with the at least two, single-element transducers rotating;

FIG. 6 illustrates an example of the three-dimensional ultrasound probe;

DETAILED DESCRIPTION

Figure 1:
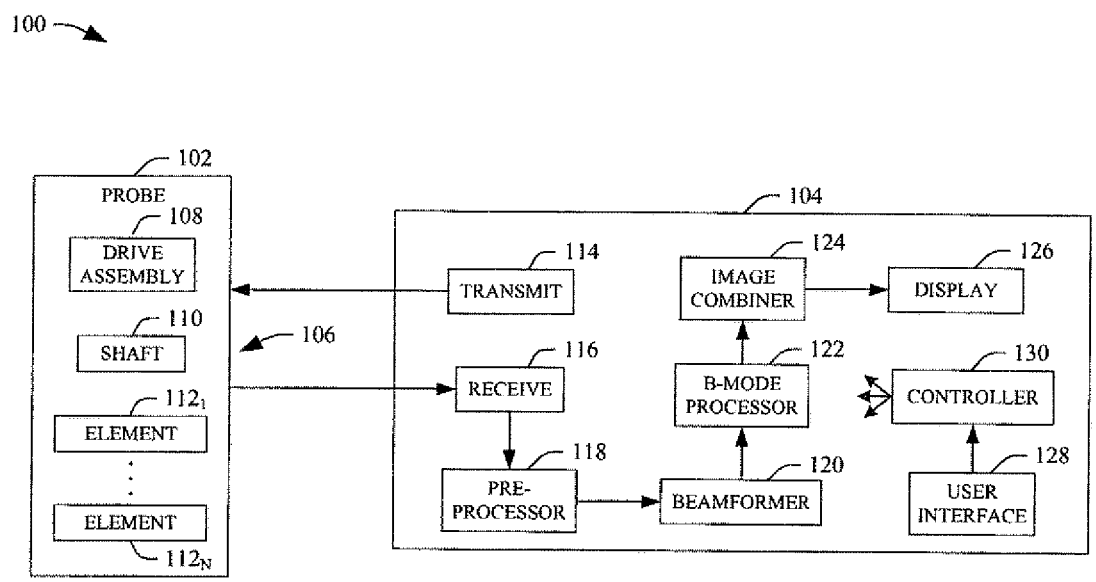
FIG. 1 schematically illustrates an example three-dimensional ultrasound probe with at least two, single-element transducers and an ultrasound imaging system configured for synthetic aperture focusing.

FIG. 1 illustrates an example imaging system 100 such as an ultrasound imaging system. The imaging system 100 includes a transducer probe 102 and an ultrasound console 104, which interface through suitable complementary hardware and/or wireless interfaces (not visible).

Figure 2:
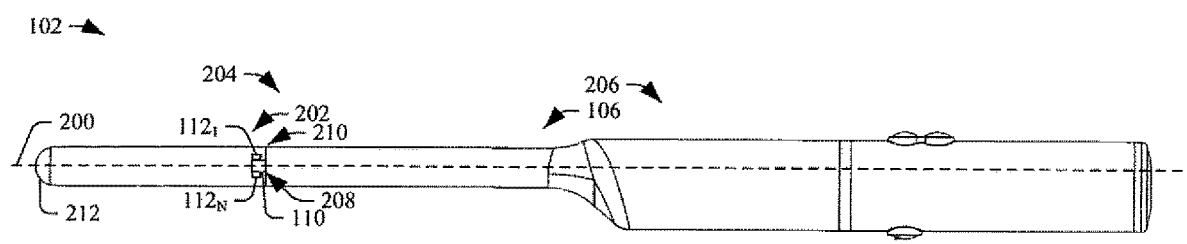
FIG. 2 schematically illustrates an example of the three-dimensional ultrasound probe with the at least two, single-element transducers in a retracted position.

The transducer probe 102 includes an elongate tubular portion 106, a drive assembly 108, an elongate shaft 110, and a plurality of single-element transducers $112_1, \ldots, 112_N$ (collectively referred to herein as single-element transducers 112), where N is a positive integer. FIG. 2 shows a non-limiting example of the transducer probe 102. In the example of FIG. 2, the elongate tubular portion 106 extends in a direction away from a handle region 206 and along a longitudinal axis 200 of the probe 102 and includes a first end region 202 and a second region 204, which is between the first end region 202 and the handle region 206. The first end region 202 includes an acoustic window.

A first end (not visible) of the shaft 110 is coupled to the drive assembly 108 (not visible), which is configured to rotate and/or translate the shaft 110. The drive assembly 108 can be in the shaft 110, the handle 206, and/or elsewhere. A second end 208 of the shaft 110 is in the first end region 202. The single-element transducer $112_1$ is coupled to the second end 208, with its transducing region perpendicular to and away facing away from the longitudinal axis 200. With a two, single-element transducer configuration (N=2), the single-element transducer $112_N$ is likewise coupled to the second end 208, but angularly shifted or offset relative to the single-element transducer $112_1$.

For instance, in the illustrated instance, the single-element transducers $112_1$ and $112_N$ are diametrically opposed, or offset one hundred and eighty degrees (180°) around the shaft 110. In another instance, the single-element transducers $112_1$ and $112_N$ are perpendicular, or offset ninety degrees (90°) around the shaft 110. In another instance, the single-element transducers $112_1$ and $112_N$ are offset sixty degrees (60°) around the shaft 110. In general, the single-element transducers $112_1$ and $112_N$ are angularly offset or separated by a single angle in a range from sixty (60) to one hundred and eighty (180) degrees. More than two, single-element transducers (i.e., N>2) are contemplated herein and can increase the frame rate. Smaller non-zero angles are also contemplated herein.

Figure 3:
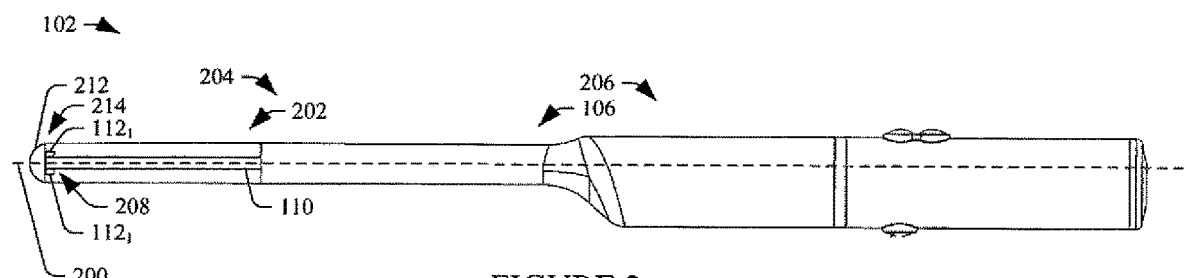
FIG. 3 schematically illustrates an example of the three-dimensional ultrasound probe with the at least two, single-element transducers in an extended position.

In FIG. 2, the shaft 110 is in a retracted position 210 with the single-element transducers $112_1$ and $112_N$ closer to the second region 204 than a tip 212 of the first region 202. In FIG. 3, the shaft 110 is in an extended position 214 with the single-element transducers $112_1$ and $112_N$ closer to the tip 212 than the second region 204. The shaft 110 is configured to translate between the retracted and extended positions 210 and 214 and, concurrently and/or independently, rotate. The rotation can be less than three hundred and sixty degrees (360°), equal to 360° (i.e., one revolution), or greater than 360° (i.e., more than one revolution). The single-element transducers 112 can acquire data for 3-D imaging while translating and rotating.

FIG. 4 shows translational movement 402 from the extended position 214 towards the retracted position 210. FIG. 4 also shows conductive paths 404 configured to route signals to and from the single-element transducers $112_1$ and $112_N$. FIG. 5 shows rotational counter-clockwise movement 502. Clockwise movement is also contemplated herein. Continuous combined translation along the sagittal plane and rotation in the transverse plan provides a helical trajectory. FIGS. 4 and 5 also show individual field of views 406 and 408 with different center frequencies, one for a nearer field (higher center frequency) and one a farer field (lower center frequency).

Returning to FIG. 1, the single-element transducers $112_1$ and $112_N$ convert an excitation electrical (e.g., pulsed) signal to an ultrasound pressure field, and receive echo signals and generate radio frequency (RF) signals indicative thereof. The echo signals, e.g., are generated in response to the transmitted pressure field interacting with structure, stationary and/or moving. The single-element transducers $112_1$ and $112_N$ can concurrently or independently transmit and receive. Transmit circuitry 114 generates the excitation electrical signal and controls the center frequency. Receive circuitry 116 receive the RF signals and, optionally, amplifies and/or digitizes them. The transmit and receive circuitry 114 and 116 transmit and receive so that data suitable for adaptive synthetic aperture focusing is acquired.

A suitable frequency range for the transducers 112 is from three (3) MHz to fifty (50) MHZ, such as eight (8) to ten (10) MHZ, or higher or lower, with a bandwidth of 60 to 75%. In one instance, the single-element transducers $112_1$ and $112_N$ respectively transmit with a center frequency at five (5) megahertz (MHz) and fifteen (15) MHz, with no overlap in their frequency bands. In this configuration, with a bandwidth of 60%, the single-element transducers $112_1$ and $112_N$ transmit in bands of 3.5 to 6.5 MHz and 10.5 to 19.5 MHz. In another instance, the frequency bands overlap less than 50%. For example, with center frequencies at 10 and 15

MHz, and a bandwidth of 70%, the single-element transducers $112_1$ and $112_N$ respectively transmit in bands of 6.5 to 13.5 MHz and 9.75 to 20.25 MHz.

A non-limiting example of the probe 102 is the 20R3 Transducer, which is a product (#9052) of BK Ultrasound, a company of Analogic Corporation, which is headquartered in Peabody, Mass., USA. FIG. 6 shows the 20R3 Transducer, including the first region 202 in which the shaft 110 (not visible) and single-element transducers 112 translate and rotate. FIG. 6 also shows control buttons 602 (e.g., forward/in, backwards/out, start/stop/capture, etc.) and a sub-portion of a cable interface 604, which includes an electro-mechanical interface (not shown), which connects to a complementary electro-mechanical interface (not shown) of the console. This probe is further discussed in BK Ultrasound, 20R3 Transducer, User Guide, February 2015.

Returning to FIG. 1, a pre-processor 118 pre-processes the RF signal. In this example, the pre-processer 118 is configured to provide standard signal conditioning for RF signals. In one instance, this includes one or more of band-pass filtering as a function of depth, separation of harmonic frequencies, shifting the center frequency to 0 (generation of in-phase and quadrature-phase (IQ) baseband signals). This may also include generating IQ data by converting the RF-signal to the complex-value IQ domain. This can be achieved, e.g., by multiplying the RF-signal by a complex sinusoid signal, e.g., I=RF×cos (wt), and Q=RF×−sin (wt). The data can be further processed, e.g., low pass filtered, decimated, etc. This processing is optional, and can be turned on or off. In a variation, the pre-processor 118 is omitted.

A beamformer 120 is configured to beamform the signals. In one instance, this includes, e.g., delay and weighting, and summing the delayed and weighted signals. As described in greater detail below, the beamformer 120, in one instance, includes a synthetic aperture beamformer configured to perform adaptive synthetic aperture focusing. In general, this beamformer corrects calculated delays, which are subject to errors due to jitter from the mechanical movement of the shaft 110, employs the corrected delays, and adaptively sums the weighted and delayed signals based on a correlation of the signals. The adaptive synthetic aperture focusing described herein can mitigate error in the position of the transducer from jitter and transducer acceleration, improving image quality.

A B-mode processor 122 processes the output of the beamformer 120. In one instance, this includes detecting the envelope of the signal and/or applying dynamic range compression (DRC) to the envelope, including thresholding. The B-mode processor 122 can process RF data and/or IQ data for generating envelope data. The DRC applied by the B-mode processor 122 can follow a linear law, a quadratic law, a logarithmic law, a μ-law and/or other DRC algorithm. The B-mode processor 122 can log compress the envelope data into a grayscale format, downscale the compressed data, and/or otherwise processes the data.

An image combiner 124 combines images from B-mode processor 122, which includes an image generated with data acquired by each of the transducer elements $112_1, \ldots, 122_N$. As described in greater detail below, the image combiner 124, in one instance, frequency compounds or blends these images from B-mode processor 122. Such compounding may first include aligning/registering the images and then combing aligned/registered images, which are acquired at different frequencies and at different spatial positions. This reduces speckle. The effect of the operation is a combined spatial and frequency compounding. The frequency compounding stems from the different bands at which the transducers operate, and the spatial compounding stems from different positions that the two transducers (relative to each other) scan the same tissue. A display 126 displays the compounded image.

A user interface (UI) 128 includes one or more input devices (e.g., a button, a knob, a slider, a touch pad, a mouse, a trackball, a touch screen, etc.) and/or one or more output devices (e.g., a display screen, a light, an audio generator, etc.), which allow for interaction between a user and the ultrasound imaging system 100. This includes allowing the sonographer to select adaptive synthetic aperture focusing. An example of monostatic synthetic aperture focusing is discussed at least in Andresen et al., "Synthetic aperture focusing for a single element transducer undergoing helical motion," IEEE transactions on ultrasonics, ferroelectrics, and frequency control, 58(5):935-43, May 2011.

A system controller 130 is configured to control one or more of the components of the console 104, the transducer elements 112, and/or other device. For example, in one instance, the system controller 130 controls the transmit circuitry 114 and/or received circuitry 116 to control the transmit angles, transmit energies, transmit frequencies, transmit and/or receive delays, weights, etc. The system controller 130 also controls beamformer 120 to perform adaptive synthetic aperture focusing and/or frequency compounding. Such control can be based on configuration files, user input, a selected mode of operation, etc.

One or more of the components of the console 104 can be implemented via one or more processors (central processing unit (CPU), graphics processing unit (GPU), microprocessor, controller, etc.) executing one or more computer readable instructions encoded or embedded on computer readable storage medium, which is a non-transitory medium such as physical memory or other non-transitory medium, and excludes transitory medium. Additionally, or alternatively, at least one of the instructions can be carried by a carrier wave, a signal, or other transitory medium.

The ultrasound imaging system 100 can be part of a portable system on a stand with wheels, a system residing on a tabletop, and/or other system in which the transducer elements 112 is housed in a probe or the like, and the console 104 is housed in an apparatus separate therefrom such as a standard and/or other computer. In another instance, the transducer elements 112 and the console 104 can be housed in a same apparatus such as within a single enclosure hand-held ultrasound scanning device.

Figure 7:
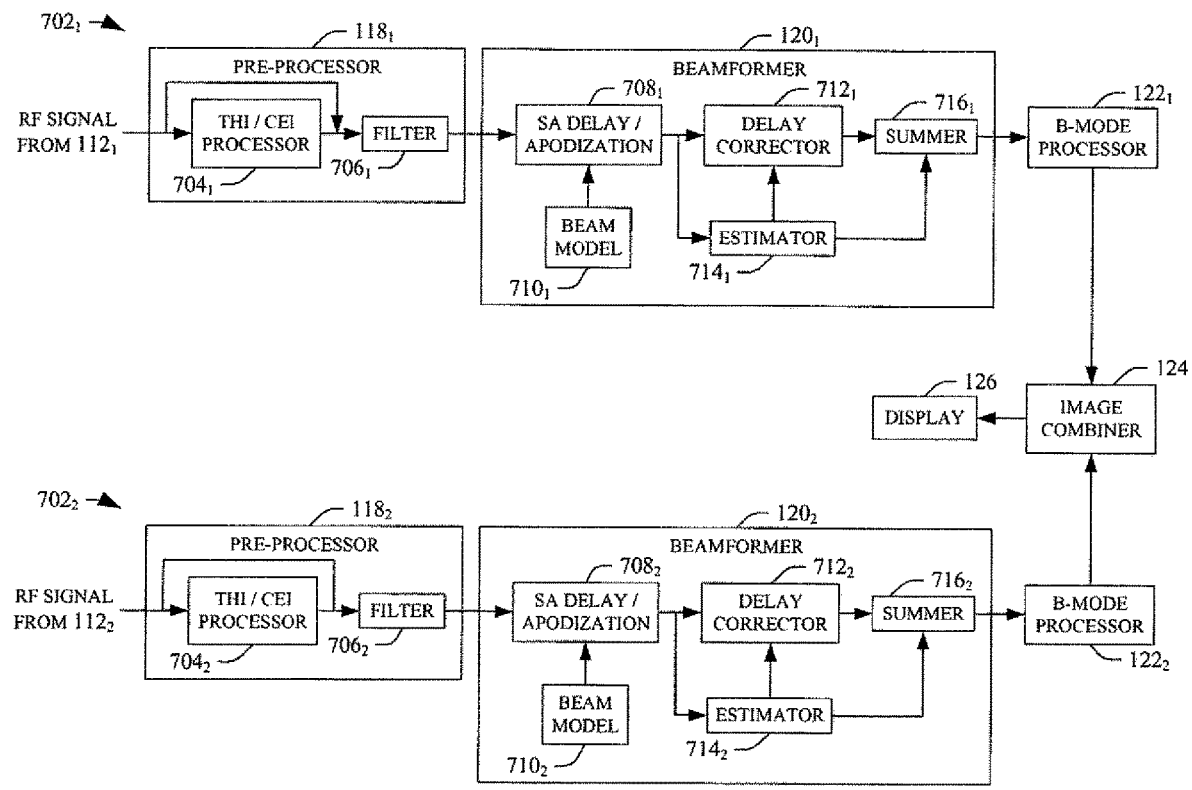
FIG. 7 illustrates an example processing chain for a two, single-element transducer configuration, including pre-processing, adaptive beamforming, post-beamforming processing, and final image construction.

FIG. 7 illustrates an example of the beamformer 120 (in connection with various other components of the system 100) for a two, single-element transducers 112 configuration. Configurations for 3, 4, 5, 6, etc. single-element transducer embodiments are also contemplated herein with some examples provided below.

A first processing chain $702_1$ processes signals from the transducer element $112_1$, and a second processing chain $702_2$ processes signals from the transducer element $112_2$. A 3, 4, 5, 6, etc. transducer configuration will have 3, 4, 5, 6, etc. processing chains, or a different processing chain for each of the single-element transducers 112. The first processing chain $702_1$ is described in detail herein. It is to be appreciated that the second (and 3, 4, 5, 6, etc.) processing chain(s) $702_2$ is identical to the first processing chain $702_1$ but processes an input signal from a different single-element transducer 112.

The first processing chain $702_1$ includes a pre-processor $118_1$, a beamformer $120_1$, and a B-mode processor $122_1$. The second processing chain $702_2$ includes a pre-processor $118_2$, a beamformer $120_2$, and a B-mode processor $122_2$. The pre-processor 118 comprises the pre-processors $118_1$ and $118_2$, the beamformer 120 comprises the beamformers $120_1$ and $120_2$, the B-mode processor 122 comprising the B-mode processors $122_1$ and $122_2$. Alternatively, these can be separate and distinct components. The processing chains $702_1$ and $702_2$ share the image combiner 124.

The illustrated pre-processer $118_1$ includes a tissue harmonic imaging (THI)/contrast enhanced imaging (CEI) processor $704_1$. The THI/CEI processor 704 implements one or more existing and/or other approaches to separate harmonic frequencies, e.g., pulse inversion, amplitude modulation, and two filters, one for the fundamental and another for the harmonic frequencies. The output signal can be either a real signal or a complex (IQ) signal, centered around a frequency in the MHz range, or around 0 Hz (baseband). In general, the signal contains both magnitude and phase information for the received echoes.

The pre-processer $118_1$ additionally or alternatively includes a filter $706_1$. In this example, the filter $706_1$ is a bandpass/sliding filter. The bandpass/sliding filter $706_1$ is used to increase signal-to-noise ratio and to separate signals with different frequency contents. The filter coefficients are updated as of function of depth to change the center frequency and the bandwidth of the filter. The output signal can be either a real signal or a complex signal. In general, the signal contains both magnitude and phase information and can be used for beamforming.

The beamformer $120_1$ includes a synthetic aperture (SA) delay/apodization processor $708_1$, a beam model $710_1$, a delay corrector $712_1$, an estimator $714_1$, and a summer (adder) $716_1$.

The SA delay/apodization processor $708_1$ processes the RF signal and/or the pre-processed signal, producing delayed signals $y_n(\vec{r})$ as shown in Equation 1:

$$y_n(\vec{r})=a_n(\vec{r})s_n(T_n(\vec{r})), \quad \text{Equation 1:}$$

where $s_n(\ )$ is a signal recorded at emission n, $T_n(\vec{r})$ is a propagation time from a surface of the single-element transducer $112_1$ to a point $\vec{r}$ and back to the single-element transducers $112_1$, and $a_n(\vec{r})$ is a weight (apodization) applied on the signal, e.g., to minimize side lobes and eliminate regions that are not illuminated by the beam. The signal $s_n(t)$ is discrete, and if $T_n$ falls between samples, then $\hat{s}_n(T_n)$ is generated by interpolation. The interpolation can be linear, spline, polynomial, based on fractional delay filters, etc.

The beam modeler $710_1$ calculates the propagation times $T_n(\vec{r})$ and the weight coefficients $a_n(\vec{r})$. The calculation of $T_n$ and $a_n$ can be based on a virtual source model, a semi-analytic model, simulated or measured data, etc. A virtual source model is discussed in Andresen et al., "Synthetic aperture focusing for a single element transducer undergoing helical motion," IEEE transactions on ultrasonics, ferroelectrics, and frequency control, 58(5):935-43, May 2011, and Frazier et al., "Synthetic aperture techniques with a virtual source element," IEEE Transactions on Ultrasonics, Ferroelectrics and Frequency Control, 45(1):196-207, 1998, etc.

A semi-analytic model is discussed in Jensen et al., "Spatial filters for focusing ultrasound images," IEEE Ultrasonics Symposium, Proceedings, An International Symposium (Cat. No. 01CH37263), Volume 2, pp. 1507-1511. IEEE, 2001. A semi-analytic model is discussed in Hansen et al. "Synthetic aperture imaging using a semi-analytic model for the transmit beams," Medical Imaging 2015: Ultrasonic Imaging and Tomography, volume 1, page 94190K, March 2015, and Nikolov et al. "Synthetic aperture imaging using a semi-analytic model for the transmit beams," IEEE International Ultrasonics Symposium (IUS), pages 1-4. IEEE, October 2015.

SA delay/apodization processor $708_1$ outputs the delayed signal $y_n$ and/or the input signal $s_n$ and the delay and weight information $T_n$, and $a_n$. The delay corrector $712_1$ and the estimator $714_1$ correct the delay $T_n$. The mechanical movements of the single-element transducers 112 gives rise to imprecisions and jitter, which introduce error in the propagation times $T_n$. The delay corrector $712_1$ interpolates a desired sample at time instance $T_n(\vec{r})+\delta_n(\vec{r})$, where $\delta_n(\vec{r})$ is a delay adjustment determined by the estimator $714_1$. An example of a suitable interpolation is discussed in Lakso et al., "Splitting the unit delay," IEEE Sig. Proc. Mag., 13(1): 30-60, 1996. Other interpolation approaches are also contemplated herein.

Figure 13:
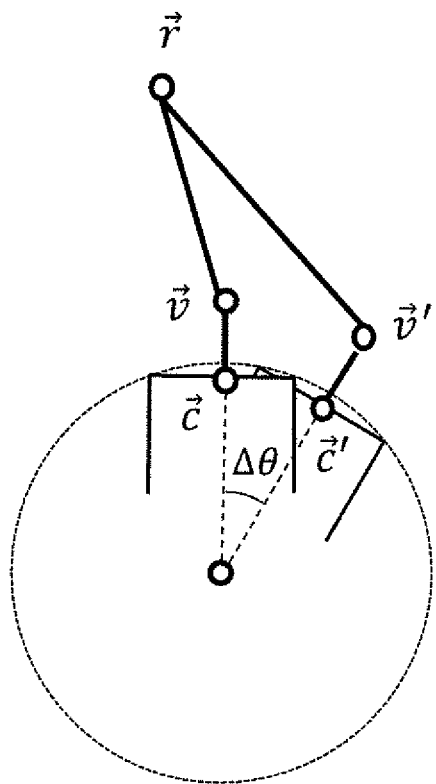
FIG. 13 depicts effects of mechanical jitter.

The estimator $714_1$ determines differences between the calculated time of flights and generates the correction value $\delta_n(\vec{r})$ based thereon. An example of generating the correction value is described in connection with FIG. 13. FIG. 13 illustrates the effects of mechanical jitter for a rotational component of motion. A difference in the angular position of the transducer is $\Delta\theta$ between the expected and the actual angle. For sharply focused transducers, the virtual source model predicts that the propagation of the sound from the transducer surface to a point in the image $\vec{r}$ follows the path $\vec{c} \rightarrow \vec{v} \rightarrow \vec{r}$, where $\vec{c}$ is the geometric center of the circular transducer and $\vec{v}$ is the focus point.

The propagation time from the transducer surface to a point P and back is defined (the subscript n for emission number is omitted for conciseness) as shown in Equation 2:

$$T(\vec{r}) = \frac{2}{c} \cdot (|\vec{v}-\vec{c}| + |\vec{r}-\vec{v}|), \quad \text{Equation 2}$$

where c is the speed of sound, and $|\vec{v}-\vec{c}|$ and $|\vec{r}-\vec{v}|$ are the lengths of the line segments connecting the respective points.

The real propagation time is as shown in Equation 3:

$$T(\vec{r}) = \frac{2}{c} \cdot (|\vec{v}'-\vec{c}'| + |\vec{r}-\vec{v}'|), \quad \text{Equation 3}$$

where $\vec{c}'$ and $\vec{v}'$ are the actual positions of the transducer center and focus points, respectively. The actual propagation time can be expressed as shown in Equation 4:

$$T'(\vec{r})=T(\vec{r})+\delta_n(\vec{r}), \quad \text{Equation 4:}$$

where $\delta_n(\vec{r})$ is the difference in arrival time due to the jitter in mechanical position, which in FIG. 13, is due to difference in angle $\Delta\theta$. The received complex signal s(t) from a point scatterer can be expressed as shown in Equation 5:

$$s(t)=A(t)\cdot e^{(-j2\pi f_0 t)}, \quad \text{Equation 5:}$$

where A(t) is an envelope function such as Gaussian, $f_0$ is a carrier frequency, and t is time. The duration of A(t) is several periods of the carrier signal. For mathematical convenience, it is often approximated with a rectangular window as shown in Equation 6:

$$A(t) = \begin{cases} 1, & -T_p/2 < t < T_p/2 \\ 0, & \text{otherwise,} \end{cases} \quad \text{Equation 6}$$

where $T_p$ is the duration of a pulse.

After delaying the signals with a delay calculated using the beam model, the signal can be expressed as shown in Equation 7:

$$\begin{aligned} y(\vec{r}) &= s(t - T'^{(\vec{r})} + T(\vec{r})) \\ &= s(t - \delta_n(\vec{r})) \\ &= A(t - \delta_n(\vec{r}))e^{(-j2\pi f_0(t - \delta_n(\vec{r})))} \end{aligned} \quad \text{Equation 7}$$

The signal y( ) whose direction (assumed direction) coincides with the line in the image that is currently beamformed (the line on which the point $\vec{r}$ is located), is used as a reference signal $y_0(\vec{r})$. This signal, for this line, is assumed not to have any jitter (all $\_\delta_0(\vec{r})$ are set to zero). All other signals are aligned to it.

To find the deviation in propagation, the cross correlation between the central signal $y_o(\vec{r})$ and the other signals $y_n(\vec{r})$ that are used in the synthetic aperture focusing are calculated at lag 0. The signals are first delayed according to the beam model, and then, their delayed versions are correlated as shown in Equation 8:

$$\begin{aligned} R_n(0, \vec{r}) &= \frac{\langle y_0(\vec{r}) y_n(\vec{r}) \rangle}{\|y_0(\vec{r})\| \|y_n(\vec{r})\|} \\ &= |R_n(0)|e^{(-j2\pi f_0 \delta_n(\vec{r}))}, \end{aligned} \quad \text{Equation 8}$$

where $y_o$ is a central beam, $y_n$ is a beam for which a weight has been calculated, $\langle \cdot ; \cdot \rangle$ is an inner product, and $\|\cdot\|$ is a norm.

The delay $\_\delta_n(\vec{r})$ is derived from the angle of the correlation function $R_n(0, \vec{r})$ as shown in Equation 9:

$$S_n(\vec{r}) = \frac{1}{2\pi f_0} \angle(R_n(0, \vec{r})). \quad \text{Equation 9}$$

This estimation procedure is based on a phase-shift technique, used in color flow imaging, and discussed in Kasai et al., "Real-Time Two-Dimensional Blood Flow Imaging Using an Autocorrelation Technique," IEEE Trans. Son. Ultrason., SU-32(3):458-464, 1985.

An alternative approach is to calculate the cross-correlation $R_n(k, \vec{r})$ for a series of lags k and search for the location of the peak of $|R_n(0, \vec{r})|$. This the approach is used for combined motion compensation and motion estimation in Nikolov et al., "Velocity estimation using recursive ultrasound imaging and spatially encoded signals," In 2000 IEEE Ultrasonics Symposium, Proceedings, An International Symposium (Cat. No. 00CH37121), volume 2, pages 1473-1477. IEEE, 2000.

The difference in the current context is that the devia tions $\_\delta_n(\vec{r})$ are due to difference in transducer position. This means that $\_\delta_n(\vec{r})$ is a systematic error for a given set of acquisitions. It is possible to find the deviation in position $\vec{c}'-\vec{c}$, as least squares fit from the beam model and the estimated deviations $\_\delta_n$. This procedure makes the estimator robust to deviations due to speckle artifacts. The procedure is further enhanced by estimating the signal to noise ratio (SNR), and using only the portions with high SNR in the least squares fit.

Figure 14:
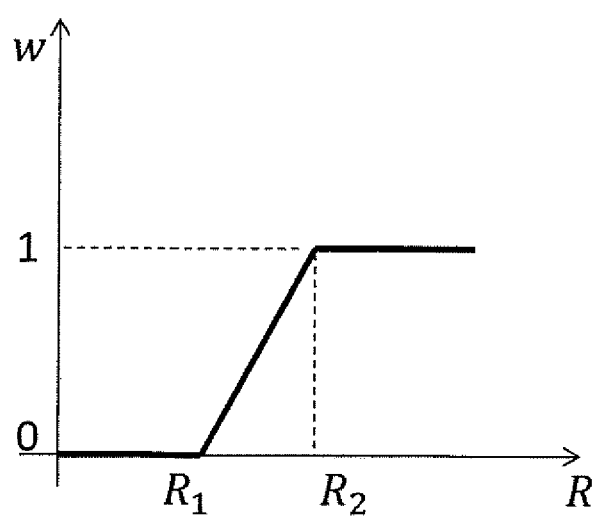
FIG. 14 shows derivation of weight coefficients for adaptive sum from the magnitude of the cross-correlation function.

The summer $716_1$ adaptively adds the delay corrected signals, which reconstructs a signal $p(\vec{p})$ at a point at a location $\vec{r}=[x,y,z]^T$. In one instance, this is achieved as shown in Equation 10:

$$p(\vec{p}) = \sum_{n=0}^{N-1} a_n(\vec{r}) w_n(\vec{r}) s_n(T_n(\vec{r}) + \delta_n(\vec{r})), \quad \text{Equation 10}$$

where N is a total number of contributing emissions, and $w_n(\vec{r})$ is a weighting coefficient. The adaptive sum ensures that the summed signals are in phase. The adaptive weight coefficient $w_n(\vec{r})$ can be computed from the magnitude of the normalized cross correlation function at lag 0 as shown in Equation 11:

$$w_n(\vec{r}) = F(|R_n(0, \vec{r})|), \quad \text{Equation 11:}$$

where F( ) is a function, and $R_n($ ) is calculated using Equation 8. An example of a suitable function F( ) is shown in FIG. 14 and Equation 12:

$$w_n(\vec{r}) = \begin{cases} 1 & |R_n(0, \vec{r})| \geq R_2 \\ \frac{|R_n(0, \vec{r}) - R_1|}{R_2 - R_1} & R_1 < |R_n(0, \vec{r})| < R_2 \\ 0 & |R_n(0, \vec{r})| \leq R_1 \end{cases} \quad \text{Equation 12}$$

For signals highly correlated signals, $w_n$ is closer to one (1), relative to less corrected signals. The function can also be sigmoid or another empirically determined relation. The calculated values of $w_n(\vec{r})$ are smoothed with a low pass filter or a polynomial fit prior to use in the adaptive sum to avoid discontinuities and/or fluctuations in the image brightness.

The B-mode processor $122_1$ processes the image generated by the summer $716_1$. As briefly discussed herein, this may include detecting the envelope and applying dynamic range compression (DRC), including thresholding. For example, the B-mode processor 122 can use IQ data for generating envelope data by computing the amplitude of the (complex) IQ signal. In another instance, the B-mode processor 122 filters the RF-data with a filter such as a finite impulse response (FIR), an infinite impulse response (IIR) filter, or other filter. The B-mode processor 122 then runs the filtered RF-data through an envelope detector.

The image combiner 124 generates a final image by (non-coherently) compounding the images from the B-mode processors $122_1$ and $122_2$. The images are misaligned due to the mechanic motion of the probe 102. The image combiner 124 aligns the images (e.g., via registration) and then adds/blends the images to create the final image. Examples of suitable compounding techniques are discussed in Gehlbach et al., "Frequency diversity speckle processing," Ultrasonic Imaging, 9(2):92-105, April 1987, and Magnin et al., "Frequency compounding for speckle contrast reduction in phased array images," Ultrasonic Imaging, 4(3):267-281, July 1982.

The image is displayed via the display 126. The approach described herein, in one instance, can achieve a uniform image before and after the focus point in the transverse plane, improve focusing in the sagittal plane, and/or reduce speckle noise. In general, this is achieved using an adaptive synthetic aperture focusing algorithm and frequency/spatial compounding. The approach is described in detail for N=2 single-element transducers, and is extended to more such as three, four (as described below), five, etc. single-element transducers 112.

Variations are described next.

Figure 8:
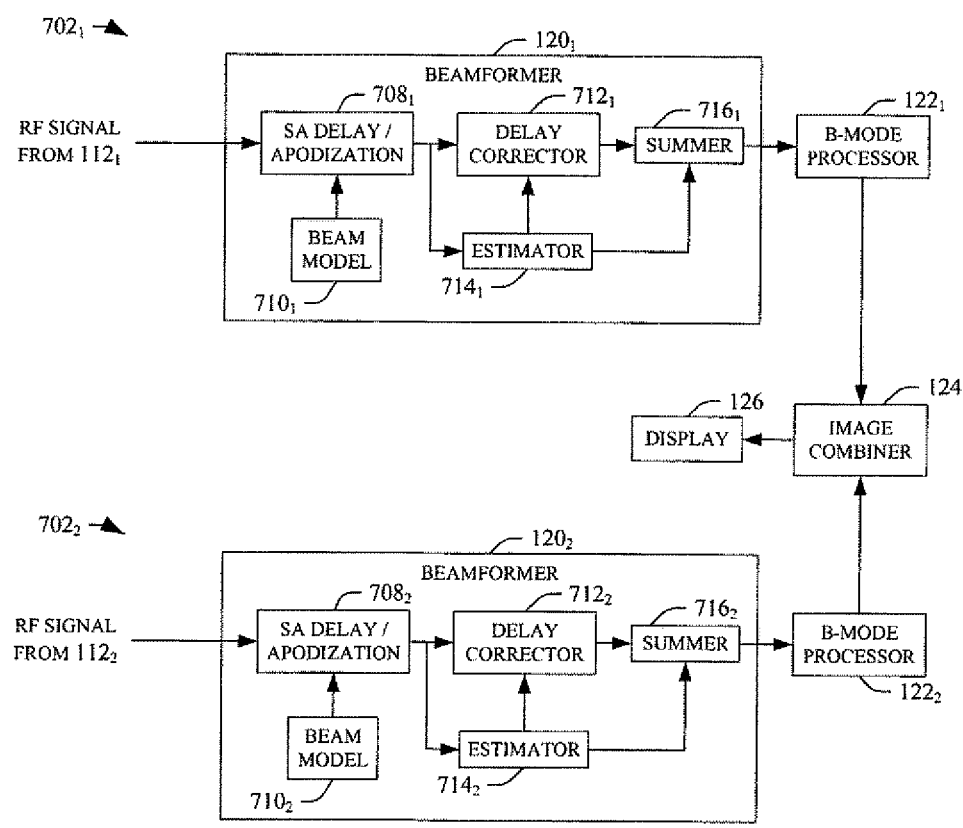
FIG. 8 illustrates a variation of FIG. 7 in which the pre-processing is omitted.

FIG. 8 is identical to FIG. 7 except the pre-processors 118 are omitted. In this instance, the beamformers 120 directly process the RF signal (or the IQ signal). This variation corrects for jitter and transducer acceleration and reduces speckle, as discussed herein and/or otherwise.

Figure 9:
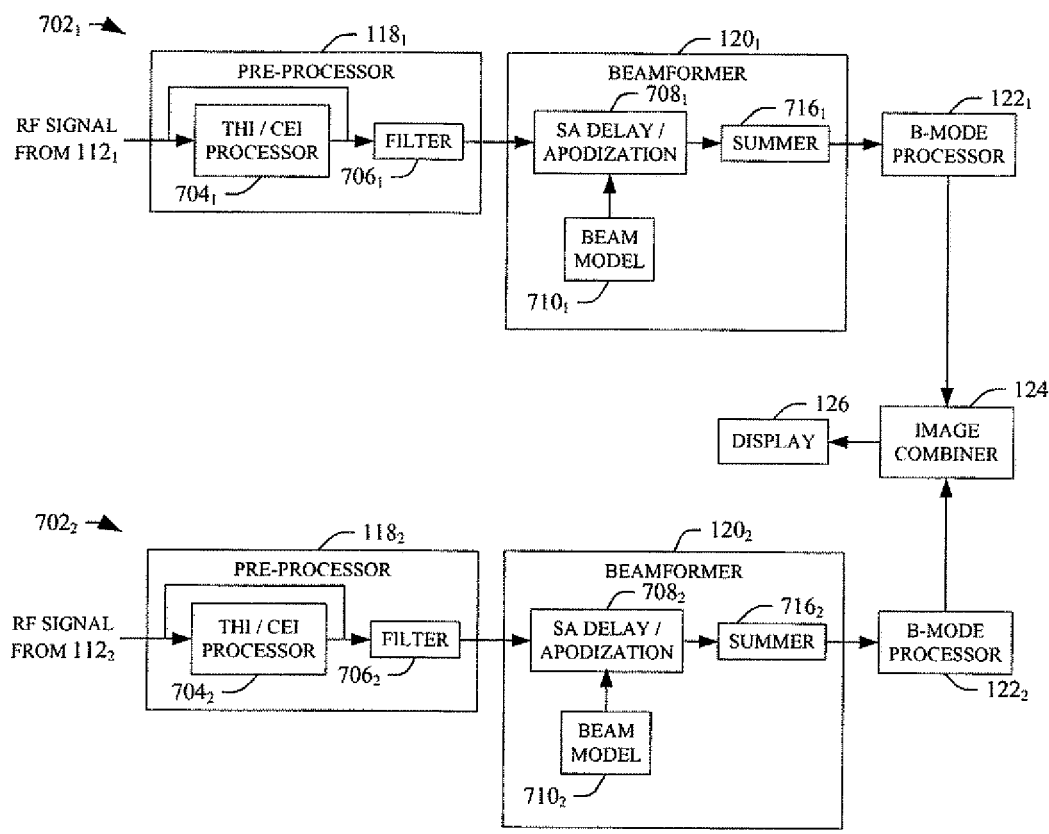
FIG. 9 illustrates a variation of FIG. 7 in which standard delay and sum beamforming is utilized.

FIG. 9 is identical to FIG. 7 except the delay corrector 712 and the estimator 714 are omitted. In this instance, the delays are not corrected before compounding. This variation reduces speckle as discussed herein. The beamformer 120 processes the input signal and reconstructs a signal $p(\vec{r})$ as shown in Equation 4:

$$p(\vec{r}) = \sum_{n=0}^{N-1} a_n(\vec{r}) s_n(T_n(\vec{r})).$$

Figure 10:
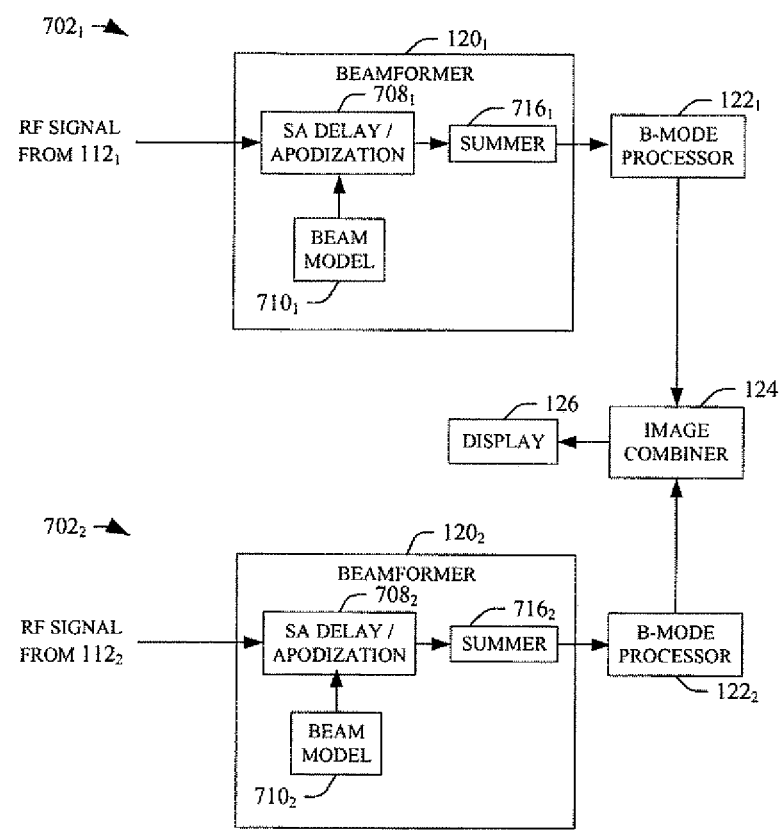
FIG. 10 illustrates a variation in which the pre-processing is omitted and standard delay and sum beamforming is utilized.

FIG. 10 is identical to FIG. 7 except the pre-processor 118, the delay corrector 712, and the estimator 714 are omitted. Similar to FIG. 8, the beamformer 120 processes the RF signal (or the IQ signal). Similar to FIG. 9, the delays are not corrected before compounding, and speckle is reduced as discussed herein and/or otherwise.

Figure 11:
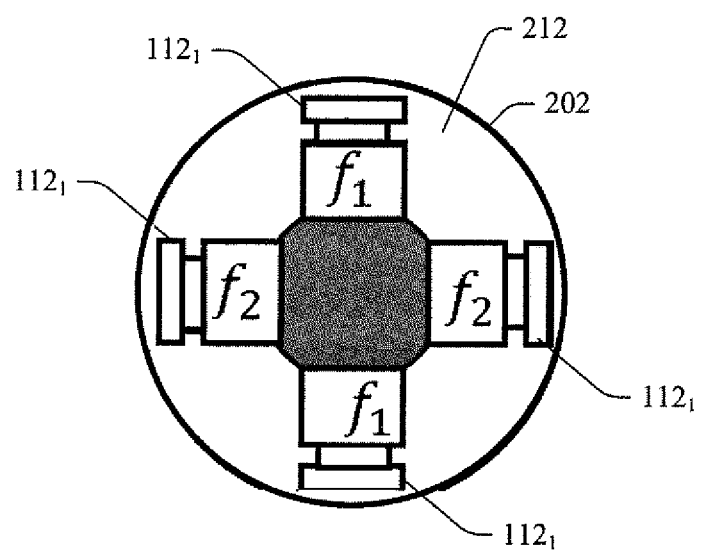
FIG. 11 schematically illustrates a variation including more than two, single-element transducers.

FIG. 11 schematically illustrates an example in which N=4.

In this example, the transducer probe 102 includes the single-element transducers $112_1$ and $112_2$ and single-element transducers $112_3$ and $112_4$. The single-element transducers $112_1$ and $112_2$ and disposed 180° apart, similar to the configuration of FIGS. 2-5. However, both of the single-element transducers $112_1$ and $112_2$ in this example, operate with the same center frequency, $f_1$. The single-element transducers $112_3$ and $112_4$ are disposed 180° apart, an angularly offset from the single-element transducers $112_1$ and $112_1$ by 90°. Both of the single-element transducers $112_3$ and $112_4$ operate with a same center frequency, $f_2$, which is different than $f_1$. Each of the single-element transducers 112 is focused. The cross-talk between the single-element transducers 112 is eliminated by their spatial position and by the different frequencies $f_1$ and $f_2$ at which they operate.

In the two, single-element transducers version described herein, the two, single-element transducers operate at two different frequency $f_1$ and $f_2$ and are focused at two different depths $z_1$ and $z_2$. In other words, there are two pairs of frequency and depth $(f_1, z_1)$ and $(f_2, z_2)$. In the four, single-element transducers version configuration, there are four pairs of frequency and depth parameters $(f_1, z_1), (f_2, z_1), (f_1, z_2),$ and $(f_2, z_2)$. The spatial and frequency separation makes it possible to acquire two or four simultaneous images with the same transmit event. The different focus depths and the different frequencies give different realizations of the speckle. The non-coherent summation of the images results in speckle reduction.

An alternative configuration is to use separate and distinct probes, each having one or more single-element transducers 112, where probes that operate at the same frequency are placed at angles of 180°.

Figure 12:
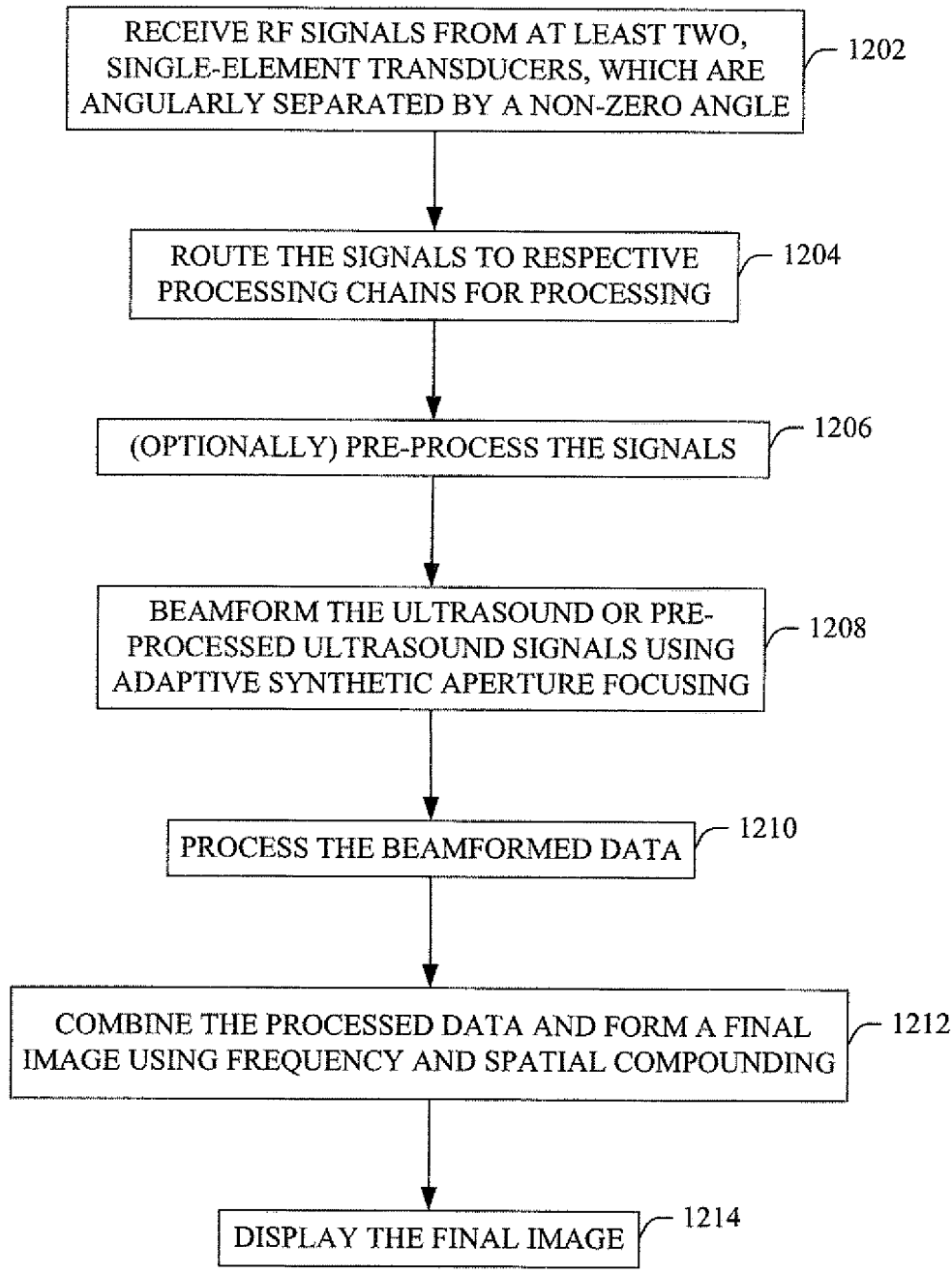
FIG. 12 schematically illustrates a method in accordance with an embodiment disclosed herein.

FIG. 12 schematically illustrates a method in accordance with an embodiment disclosed herein.

It is to be understood that the following acts are provided for explanatory purposes and are not limiting. As such, one or more of the acts may be omitted, one or more acts may be added, one or more acts may occur in a different order (including simultaneously with another act), etc.

At 1202, ultrasound signals from at least two, single-element transducers are received. As described herein, the at least two, single-element transducers operate at different center frequencies with field of views at different spatial positions (e.g., 180° apart).

At 1204, the ultrasound signals from the at least two, single-element transducers are input to respective processing chains.

At 1206, the ultrasound signals are pre-processed in their respective processing chains. In a variation, this act is omitted.

At 1208, the ultrasound or pre-processed ultrasound signals are beamformed using adaptive synthetic aperture focusing, as described herein and/or otherwise.

At 1210, the beamformed data is processed via a B-mode processor, as described herein and/or otherwise.

At 1212, the output of the B-mode processor is combined to form a final image using frequency and spatial compounding, as described herein and/or otherwise.

At 1214, the final image is displayed.

At least a portion of one or more of the methods discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The embodiments disclosed herein can be used in applications such as pelvic, prostate and/or other imaging.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method for ultrasound imaging with a first single-element transducer and a second single-element transducer, wherein the first and second single-element transducers are disposed on an ultrasound probe shaft, which has a longitudinal axis, with transducing sides disposed transverse to and facing away from the longitudinal axis, the first and second single-element transducers are angularly offset from each other on the shaft by a non-zero angle, the method, comprising:
    operating the first and second single-element transducers at first and second different cutoff frequencies;
    concurrently translating and rotating the shaft, moving the first and second single-element transducers along a helical path while the first and second single-element transducers acquire first and second echo signals;
    receiving first electrical signals from the first single-element transducer, wherein the first electrical signals are indicative of the first echo signals, and receiving second electrical signals from the second single-element transducer, wherein the second electrical signals are indicative of the second echo signals;

delay and sum beamforming, with first and second adaptive synthetic aperture focusing beamformers, the first and second electrical signals, respectively via different processing chains, employing adaptive synthetic aperture focusing, producing first and second images, wherein the delay and sum beamforming is based on a cross-correlation function:

$$\frac{\langle y_0(\vec{r}) y_n(\vec{r}) \rangle}{\|y_0(\vec{r})\| \|y_n(\vec{r})\|}$$

where $y_o$ is a central signal, $y_n$ is a signal of the delayed electrical signals, $\langle \cdot ; \cdot \rangle$ is an inner product, and $\|\cdot\|$ is a norm;

combining the first and second images, creating a final image, which has reduced speckle noise and higher contrast resolution relative to the first and second images; and displaying the final image.

2. The method of claim 1, wherein the adaptive synthetic aperture focusing corrects calculated first and second delays for transducer position errors with first and second corrections, weights and delays the first and second electrical signals with first and second weights and the corrected calculated first and second delays, and adaptively sums the weighted and delayed first and second electrical signals respectively based on first and second adaptive weight coefficients, producing the first and second images.

3. The method of claim 2, wherein the delay and sum beamforming includes:
computing the first weights and the calculated first delays and the second weights and the calculated second delays with one of a virtual source model, a semi-analytic model, simulated data, or measured data.

4. The method of claim 2, wherein the delay and sum beamforming includes:
determining the first corrections for the calculated first delays by determining differences between the calculated first delays and adding the first corrections to the calculated first delays; and
determining the second corrections for the calculated second delays by determining differences between the calculated second delays and adding the second corrections to the calculated second delays.

5. The method of claim 2, further comprising:
determining first levels of coherence between the first corrected calculated delayed signals;
generating the first adaptive weight coefficients with the first levels of coherence;
determining second levels of coherence between the second corrected calculated delayed signals; and
generating the second adaptive weight coefficients with the second levels of coherence.

6. The method of claim 2, wherein the combining of the first and second images includes frequency compounding the first and second images.

7. The method of claim 6, wherein the combining of the first and second images includes registering the first and second images and then the frequency compounding of the first and second images.

8. The method of claim 7, wherein the combining of the first and second images includes spatially compounding the first and second images.

9. The method of claim 2, further comprising:
band-pass filtering the first electrical signals as a function of depth and band-pass filtering the second electrical signals as a function of depth and beamforming the filtered first and second electrical signals.

10. The method of claim 2, further comprising:
deriving first and second In-phase/Quadrature data respectively from the first and second electrical signals and beamforming the first and second In-phase/Quadrature data.

11. The method of claim 2, further comprising:
separating a first set and a second set of harmonic frequencies respectively from the first and second electrical signals and beamforming the first and second sets of harmonic frequencies.

12. The method of claim 2, further comprising:
shifting the first and second different cutoff frequencies and beamforming the first and second electrical signals with the shifted different cutoff frequencies.

13. The method of claim 2, further comprising:
detecting a first envelope and a second envelope respectively from the first and second beamformed signals and combining the first and second envelopes to produce the final image.

14. The method of claim 13, further comprising:
compressing the first and second envelopes and combining the first and second compressed envelopes to produce the final image.

15. The method of claim 2, wherein the delay and sum beamforming includes:
delaying the first electrical signals with first delays determined by a first beam model to generate delayed first electrical signals, wherein the first electrical signals include jitter;
determining first deviations in propagation between the delayed first electrical signals and first reference signals that do not include jitter;
determining the first corrections based on the first deviations;
delaying the second electrical signals with second delays determined by a second beam model to generate delayed second electrical signals, wherein the second electrical signals include jitter;
determining second deviations in propagation between the delayed second electrical signals and second reference signals that do not include jitter; and
determining the second corrections based on the second deviations.

16. The method of claim 15, wherein the delay and sum beamforming includes:
determining the first deviations by cross-correlating central signals of the first reference signals with the delayed first electrical signals; and
determining the second deviations by cross-correlating central signals of the second reference signals with the delayed second electrical signals.

17. The method of claim 16, wherein the deviations are due to a difference in transducer position.

18. The method of claim 1, wherein the delay and sum beamforming includes:
deriving the first corrections from a first angle of the correlation function; and
deriving the second corrections from a second angle of the correlation function.

19. The method of claim 1, wherein the first deviations and the second deviations represent systematic error for given sets of acquisitions.

20. The method of claim 1, wherein the delay and sum beamforming includes:
computing the first and second weights using:

$$F(|R_n(0,\vec{r})|)$$

where F( ) is:

$$\begin{cases} 1 & |R_n(0,\vec{r})| \geq R_2 \\ \dfrac{|R_n(0,\vec{r})-R_1|}{R_2-R_1} & R_1 < |R_n(0,\vec{r})| < R_2 \\ 0 & |R_n(0,\vec{r})| \leq R_1 \end{cases}$$

and $R_n(0,\vec{r})$ is the correlation function.

21. The method of claim 2, wherein the delay and sum beamforming includes:
computing the weights for the first and second electrical signals from magnitudes of normalized cross correlation functions at lag 0.

22. The method of claim 1, further including:
receiving one or more electrical signals from one or more single-element transducers;
delay and sum beamforming, with one or more adaptive synthetic aperture focusing beamformers, the one or more electrical signals, respectively via different processing chains, employing adaptive synthetic aperture focusing, producing one or more images; and
combining the first, second and one or more images, creating the final image.

23. The method of claim 1, wherein the adaptive synthetic aperture focusing corrects calculated first and second delays for transducer position errors with first and second corrections.

24. The method of claim 23, wherein the adaptive synthetic aperture focusing determines differences between calculated time of flights to determine values for the first and second corrections.

25. The method of claim 23, wherein the adaptive synthetic aperture focusing weights and delays the first and second electrical signals with first and second weights and the corrected calculated first and second delays.

26. A method for ultrasound imaging with a first single-element transducer and a second single-element transducer, wherein the first and second single-element transducers are disposed on an ultrasound probe shaft, which has a longitudinal axis, with transducing sides disposed transverse to and facing away from the longitudinal axis, the first and second single-element transducers are angularly offset from each other on the shaft by a non-zero angle, the method, comprising:
operating the first and second single-element transducers at first and second different cutoff frequencies;
concurrently translating and rotating the shaft, moving the first and second single-element transducers along a helical path while the first and second single-element transducers acquire first and second echo signals;
receiving first electrical signals from the first single-element transducer, wherein the first electrical signals are indicative of the first echo signals, and receiving second electrical signals from the second single-element transducer, wherein the second electrical signals are indicative of the second echo signals;
delay and sum beamforming, with first and second adaptive synthetic aperture focusing beamformers, the first and second electrical signals, respectively via different processing chains, employing adaptive synthetic aperture focusing, producing first and second images,
wherein the adaptive synthetic aperture focusing corrects calculated first and second delays for transducer position errors with first and second corrections, weights and delays the first and second electrical signals with first and second weights and the corrected calculated first and second delays, and adaptively sums the weighted and delayed first and second electrical signals respectively based on first and second adaptive weight coefficients, producing the first and second images,
wherein the delay and sum beamforming includes: delaying the first electrical signals with first delays determined by a first beam model to generate delayed first electrical signals, wherein the first electrical signals include jitter, determining first deviations in propagation between the delayed first electrical signals and first reference signals that do not include jitter by cross-correlating central signals of the first reference signals with the delayed first electrical signals, determining the first corrections based on the first deviations, delaying the second electrical signals with second delays determined by a second beam model to generate delayed second electrical signals, wherein the second electrical signals include jitter, by cross-correlating central signals of the second reference signals with the delayed second electrical signals, and
wherein the delay and sum beamforming is based on a cross-correlation function:

$$\frac{\langle y_0(\vec{r}) y_n(\vec{r}) \rangle}{\|y_0(\vec{r})\| \|y_n(\vec{r})\|}$$

where $y_0$ is a central signal, $y_n$ is a signal of the delayed electrical signals, $\langle \cdot ; \cdot \rangle$ is an inner product, and $\|\cdot\|$ is a norm;
combining the first and second images, creating a final image, which has reduced speckle noise and higher contrast resolution relative to the first and second images; and
displaying the final image.

* * * * *